United States Patent
Hajishah et al.

(10) Patent No.: US 10,932,950 B2
(45) Date of Patent: Mar. 2, 2021

(54) APPARATUS, SYSTEM AND METHOD OF ULTRASONIC POWER DELIVERY IN A SURGICAL SYSTEM

(71) Applicant: JOHNSON & JOHNSON SURGICAL VISION, INC., Santa Ana, CA (US)

(72) Inventors: Abraham Hajishah, Irvine, CA (US); Edith W. Fung, Diamond Bar, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 195 days.

(21) Appl. No.: 16/152,179

(22) Filed: Oct. 4, 2018

(65) Prior Publication Data
US 2019/0133824 A1    May 9, 2019

Related U.S. Application Data

(60) Provisional application No. 62/568,232, filed on Oct. 4, 2017.

(51) Int. Cl.
*A61F 9/007* (2006.01)
*A61B 34/00* (2016.01)
(Continued)

(52) U.S. Cl.
CPC .. *A61F 9/00745* (2013.01); *A61B 17/320068* (2013.01); *A61B 34/25* (2016.02);
(Continued)

(58) Field of Classification Search
CPC ............ H01H 3/14; A61B 2017/00977; A61B 2017/320084; A61B 2017/00973; A61B 34/25; A61F 9/00745
See application file for complete search history.

(56) References Cited

U.S. PATENT DOCUMENTS

| | | |
|---|---|---|
| 4,954,960 A | 9/1990 | Lo et al. |
| 5,700,240 A | 12/1997 | Barwick, Jr. et al. |
| | (Continued) | |

FOREIGN PATENT DOCUMENTS

| | | |
|---|---|---|
| IN | 201206927 | 11/2015 |
| WO | 2010054146 A1 | 5/2010 |
| | (Continued) | |

OTHER PUBLICATIONS

Ngo, W.K., et al., "Heat Profiling of Phacoemulsification Tip Using a Thermal Scanning Camera," International Ophthalmology, Dec. 2013, vol. 33(6), pp. 645-649.

(Continued)

*Primary Examiner* — Anh T Dang
(74) *Attorney, Agent, or Firm* — Johnson & Johnson Surgical Vision, Inc.

(57) ABSTRACT

The disclosed apparatus, system and method may include at least a phacoemulsification surgical console having a customizable non-linear custom phacoemulsification mode. The apparatus, system and method may include an ultrasonic delivery tip; a foot pedal; and non-transitory computing code resident on a computing memory associated with a computing processor which, when executed by the processor, causes to be executed the steps of: receiving a percentage actuation of the foot pedal; calculating, including from a non-linear algorithm, a percentage actuation for the ultrasonic delivery tip corresponded to the received percentage foot pedal actuation; and dictating the calculated percentage actuation for the ultrasonic delivery tip actuation to the ultrasonic delivery tip.

12 Claims, 3 Drawing Sheets

(51) Int. Cl.
  *A61B 17/32* (2006.01)
  *H01H 3/14* (2006.01)
  *A61B 17/00* (2006.01)
(52) U.S. Cl.
  CPC ..... *H01H 3/14* (2013.01); *A61B 2017/00199* (2013.01); *A61B 2017/00973* (2013.01); *A61B 2017/00977* (2013.01); *A61B 2017/32007* (2017.08); *A61B 2017/320069* (2017.08); *A61B 2017/320084* (2013.01)

(56) References Cited

U.S. PATENT DOCUMENTS

| | | |
|---|---|---|
| 7,785,336 B2 | 8/2010 | Staggs |
| 8,523,812 B2 | 9/2013 | Boukhny et al. |
| 8,523,813 B2 | 9/2013 | Grispo et al. |
| 8,758,433 B2 | 6/2014 | Cole et al. |
| 8,986,290 B2 | 3/2015 | Patton et al. |
| 2003/0073980 A1 | 4/2003 | Finlay et al. |
| 2012/0083800 A1 | 4/2012 | Andersohn et al. |
| 2012/0302941 A1 | 11/2012 | Teodorescu et al. |
| 2014/0276920 A1 | 9/2014 | Hendrick et al. |
| 2015/0144514 A1 | 5/2015 | Brennan et al. |
| 2016/0302816 A1 | 10/2016 | Clayton et al. |

FOREIGN PATENT DOCUMENTS

| | | |
|---|---|---|
| WO | 2011084221 A2 | 7/2011 |
| WO | 2012161913 A1 | 11/2012 |

OTHER PUBLICATIONS

International Search Report and Written Opinion for Application No. PCT/IB2018/057553, dated Dec. 14, 2018, 12 pages.

APPARATUS, SYSTEM AND METHOD OF ULTRASONIC POWER DELIVERY IN A SURGICAL SYSTEM

CROSS REFERENCES TO RELATED APPLICATIONS

This application claims the benefit under 35 U.S.C. § 119(e) of U.S. Provisional Patent Application No. 62/568,232, filed Oct. 4, 2017, which is incorporated herein by reference in its entirety.

BACKGROUND

Field of the Disclosure

The present disclosure relates to medical devices and systems, and, more specifically, to an apparatus, system and method of ultrasonic power delivery in a surgical system.

Description of the Background

Phacoemulsification is a medically recognized technique utilized for crystalline lens removal. Phacoemulsification includes making a corneal and/or scleral incision, and the insertion of a phacoemulsification handpiece, which is typically comprised of a needle that is ultrasonically driven, in order to emulsify, i.e., to liquefy, the natural crystalline lens and/or or to break a cataract into small pieces, by way of example. The emulsified pieces may subsequently be removed using the same handpiece or another handpiece. The surgeon may then insert implants in the eye through the incision.

The phacoemulsification handpiece is generally coupled to an irrigation source and an aspiration pump. The handpiece includes a distal tip for insertion within the anterior chamber of the patient's eye that emits the ultrasonic energy to emulsify the crystalline lens. The handpiece further includes an irrigation port proximal to the distal tip, which is coupled to an irrigation source via an irrigation line, and an aspiration port at the distal tip, which is coupled to an aspiration pump via an aspiration line. Fluid from the irrigation source, which is typically an elevated bottle of saline solution, is irrigated into the eye via the irrigation line and the irrigation port, and the irrigation fluid and emulsified crystalline lens material are aspirated from the eye by the aspiration pump via the aspiration port and the aspiration line.

Other medical techniques for the eye also typically include emulsifying, irrigating the eye and aspirating. Such procedures may or may not include the destruction, alteration or removal of features of the natural eye using the emulsification, irrigation and aspiration. Thus, the ultrasonic power delivered by the surgical console, and the flow of fluid to and from a patient through the irrigation or aspiration console, and the consequent need to control the phacoemulsification handpiece to deliver the foregoing, is critical to the procedure performed.

Phacoemulsification systems typically include a programmable microprocessor-based console with operator-selected presets for controlling, for example, aspiration rate, vacuum and ultrasonic power levels. The phacoemulsification handpiece may be interconnected with the control console by an electric cable for powering and controlling the piezoelectric transducer that provides the emulsification. Tubing provides the irrigation fluid to the eye, and enables withdrawal of aspiration fluid from an eye, through the handpiece under the control of the console.

Phase angles and other aspects associated with handpiece operation are determined and measured at all times during operation of the handpiece, such as to adjust the driving circuitry, achieve an optimum phase angle, and otherwise effect energy transfer into the tissue from the phacoemulsification handpiece. Automatic tuning of the handpiece may be provided by monitoring the handpiece electrical signals and adjusting the frequency and other aspects to maintain consistency with selected parameters.

Control of the ultrasonic power by the phacoemulsification handpiece is therefore highly critical to successful phacoemulsification surgery. Certain known systems address the requirements of power control for the phacoemulsification handpiece based on the phase angle between voltage applied to a handpiece piezoelectric transducer and the current drawn by the piezoelectric transducer and/or the amplitude of power pulses provided to the handpiece. The typical arrangement may be tuned for the particular handpiece, and, for example, power may be applied in a continuous fashion or in a series of solid bursts subject to the control of the surgeon. For example, the system ay apply power for 150 ms, then cease power for 350 ms, and may repeat this on/off sequence for the necessary duration of power application.

Application of power during the aforementioned 150 ms period may be defined as a constant application of a 25 kHz to 50 kHz sinusoid. In certain circumstances, the surgeon/operator may wish to apply the power bursts for a duration of time, then cease application of power, then reapply at the initial or another power setting. The frequency and duration of the burst is typically controllable, as is the length of the stream of bursts applied to the affected area. The time period where power s not applied may enable periods in which broken sections may be removed using aspiration, such as may be provided by the handpiece or a secondary aspiration apparatus.

Current control methods for ultrasonic power delivery are generally limited to two modes, referred to herein as "panel" and "linear." As to these referenced modes, the "panel" mode typically provides strict, fixed values upon user selection, and the "linear" mode allows only the simplest form of linear adjustment from 0% to 100%. Intermediate adjustments for delivery are not made freely available, in part in order to minimize the need for and risk inherent in manual adjustment.

The application of power in the aforementioned manners may, in certain circumstances, cause overheating, time lag, turbulence and/or chatter, as well as causing significant flow issues, such as requiring considerable use of fluid to relieve the area and remove particles. Also, the application of constant energy may cause fragments to be pushed away from the tip of the handpiece because of the resultant cavitation from the energy applied.

Thus, the existing methods of ultrasonic power delivery, as discussed above, are very simplistic, suffer from numerous disadvantages, and are thus not ideal in application for every eye surgery. Accordingly, new techniques other than the two existing simple methods (linear and panel) of power delivery are needed to provide advanced control methods and algorithms, such as may be used to regulate the delivery of ultrasonic power with varying rates of increase and decrease, from gradual to acute, and/or to define a sweet spot in controlling the ultrasonic power delivered.

SUMMARY

The disclosed apparatus, system and method may include at least a phacoemulsification surgical console having a customizable non-linear custom phacoemulsification mode. The apparatus, system and method may include an ultrasonic delivery tip; a footpedal; and non-transitory computing code resident on a computing memory associated with a computing processor which, when executed by the processor, causes to be executed the steps of: receiving a percentage actuation of the footpedal; calculating, including from a non-linear algorithm, a percentage actuation for the ultrasonic delivery tip corresponded to the received percentage footpedal actuation; and dictating the calculated percentage actuation for the ultrasonic delivery tip actuation to the ultrasonic delivery tip.

More particularly, a method of providing a customizable, non-linear custom mode for ultrasonic power in ophthalmic surgery may include receiving a footpedal actuation percentage from an ophthalmic surgery console; relationally comparing the footpedal actuation percentage to a non-linear custom zone algorithm which is calculated from at least one user-indicated set point for ultrasonic power corresponded to a particular one of the footpedal actuation percentage; and calculating a next one of the ultrasonic power from the custom zone algorithm.

Thus, the disclosed embodiments provide an apparatus, system, and method for providing a custom mode for vacuum and/or aspiration in a surgical system.

BRIEF DESCRIPTION OF THE FIGURES

Referring now to the figures incorporated herein, shown are non-limiting embodiments of the present disclosure, wherein like numerals represent like elements, and wherein.

DETAILED DESCRIPTION

Figure 1:
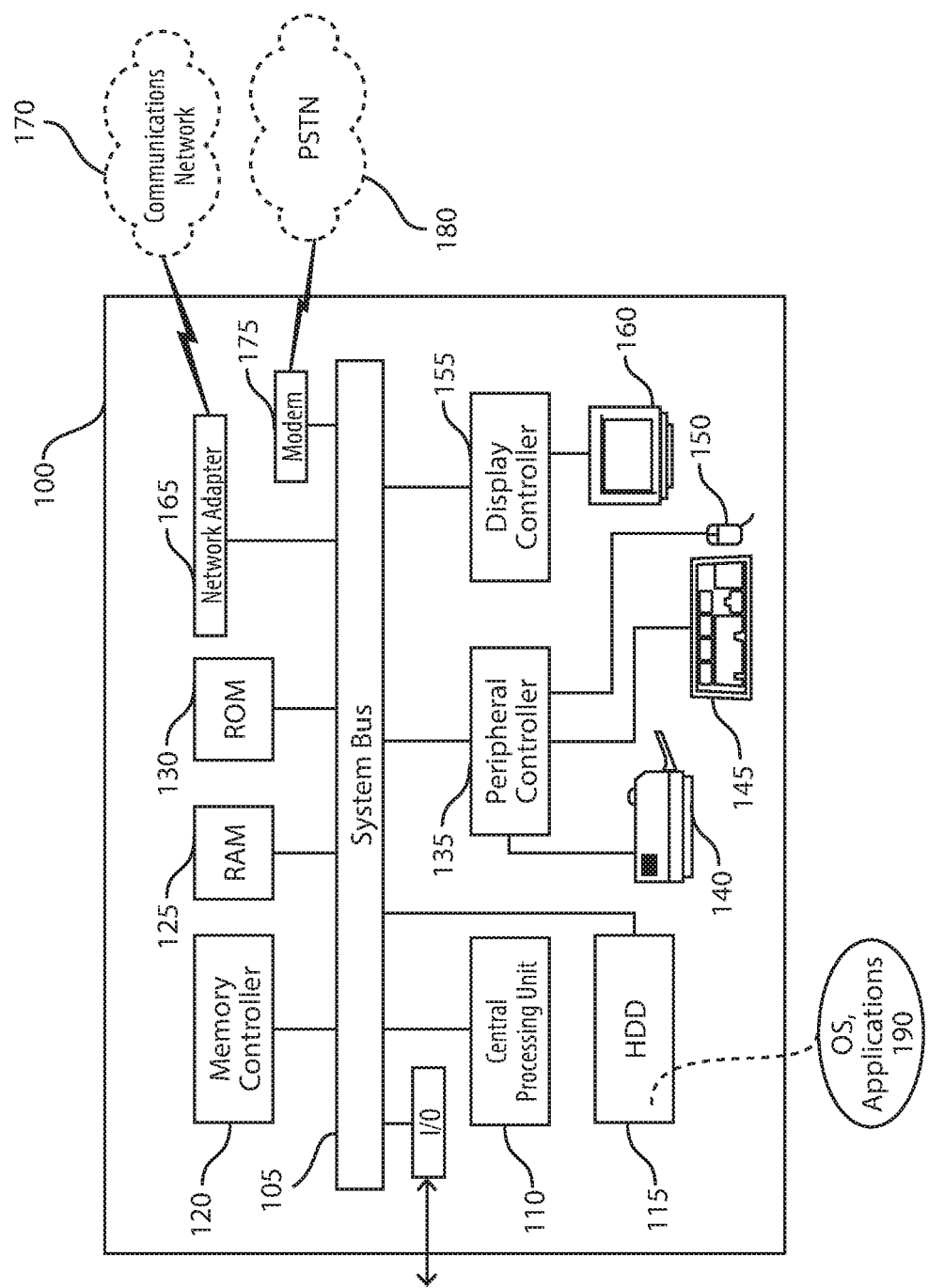
FIG. 1 is a block diagram illustrating a computing system according to the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens with a handpiece. Once the lens is emulsified, it is aspirated from the eye by applying a vacuum tube to the emulsified lens material.

To perform the afore-discussed and similar procedures, a surgeon often utilizes a computer-controlled system of specialized equipment called a phacoemulsification system to control and execute the ultrasonic emulsification and aspiration of the natural lens of the eye prior to inserting the IOL. Phacoemulsification systems use various computer programs for performing these various tasks, which are controlled in part by adjusting settings of these programs, for example, to emulsify and aspirate the subject lens material and to do other tasks necessary to complete the surgery. Different phacoemulsification systems may provide different programs for use in different situations, whereby are provided different operational modes. For example, program modes may take into account the particular subject eye on which surgery is performed such as based, for example, on measurements of the eye and various other aspects of the patient's physiology.

New alternative modes provided according to the embodiments may open up different desirable options to provide a range of different power deliveries in different modes for different cataract and/or other surgical needs. In addition, customized power delivery modes may allow for enhanced comfort in the use of peripherals to the phacoemulsification console, such as footpedals, by, for example, allowing a surgeon ease in operating in a zone of footpedal use that is most comfortable and efficient for that surgeon, and by tying that zone algorithmically to certain custom operations of the emulsifier.

Further, these new operational modes, beyond the known linear and panel modes, may overcome the inefficiencies of limited power delivery methods, slow transition between power deliveries, and difficulties in controlling and maintaining power at necessary power levels. These new modes provide advanced control methods and algorithms to regulate the delivery of power with varying rates of increase and decrease, from gradual to acute, and to define optimal power control for given circumstances.

FIG. 1 depicts an exemplary computing system 100 for use in association with an ophthalmic surgical console in accordance with herein described system and methods. Computing system 100 is capable of executing software, such as an operating system (OS) and one or more computing applications 190, such as may run the handpiece discussed herein via the I/O port. The operation of exemplary computing system 100 is controlled primarily by computer readable instructions, such as instructions stored in a computer readable storage medium, such as hard disk drive (HDD) 115, optical disk (not shown) such as a CD or DVD, solid state drive (not shown) such as a USB "thumb drive," or the like. Such instructions may be executed within central processing unit (CPU) 110 to cause computing system 100 to perform operations. In many known computer servers, workstations, personal computers, and the like, CPU 110 is implemented in an integrated circuit called a processor.

It is appreciated that, although exemplary computing system 100 is shown to comprise a single CPU 110, such description is merely illustrative, as computing system 100 may comprise a plurality of CPUs 110. Additionally, computing system 100 may exploit the resources of remote CPUs (not shown), for example, through communications network 170 or some other data communications means.

In operation, CPU 110 fetches, decodes, and executes instructions from a computer readable storage medium such as HDD 115. Such instructions may be included in software such as an operating system (OS), executable programs, and the like. Information, such as computer instructions and other computer readable data, is transferred between components of computing system 100 via the system's main data-transfer path. The main data-transfer path may use a system bus architecture 105, although other computer architectures (not shown) can be used, such as architectures using serializers and deserializers and crossbar switches to communicate data between devices over serial communication paths. System bus 105 may include data lines for sending data, address lines for sending addresses, and control lines for sending interrupts and for operating the system bus. Some busses provide bus arbitration that regulates access to the bus by extension cards, controllers, and CPU 110. Devices that attach to the busses and arbitrate access to the bus are called bus masters. Bus master support also allows multiprocessor configurations of the busses to be created by the addition of bus master adapters containing processors and support chips.

Memory devices coupled to system bus 105 may include random access memory (RAM) 125 and/or read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode may normally access only memory mapped by its own process virtual address space; in such instances, the program cannot access memory within another process' virtual address space unless memory sharing between the processes has been set up.

In addition, computing system 100 may contain peripheral communications bus 135, which is responsible for communicating instructions from CPU 110 to, and/or receiving data from, peripherals, such as peripherals 140, 145, and 150, which may include printers, keyboards, and/or the surgical elements, such as footpedals, discussed herein throughout. An example of a peripheral bus is the Peripheral Component Interconnect (PCI) bus.

Display 160, which is controlled by display controller 155, may be used to display visual output and/or presentation generated by or at the request of computing system 100, responsive to operation of the aforementioned computing program. Such visual output may include text, graphics, animated graphics, and/or video, for example. Display 160 may be implemented with a CRT-based video display, an LCD or LED-based display, a gas plasma-based flat-panel display, a touch-panel display, or the like. Display controller 155 includes electronic components required to generate a video signal that is sent to display 160.

Further, computing system 100 may contain network adapter 165 which may be used to couple computing system 100 to external communication network 170, which may include or provide access to the Internet, an intranet, an extranet, or the like. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

Network adaptor 165 may communicate to and from network 170 using any available wired or wireless technologies. Such technologies may include, by way of non-limiting example, cellular, Wi-Fi, Bluetooth, infrared, or the like.

It is appreciated that exemplary computing system 100 is merely illustrative of a computing environment in which the herein described systems and methods may operate, and does not limit the implementation of the herein described systems and methods in computing environments having differing components and configurations. That is to say, the inventive concepts described herein may be implemented in various computing environments using various components and configurations.

Figure 2:
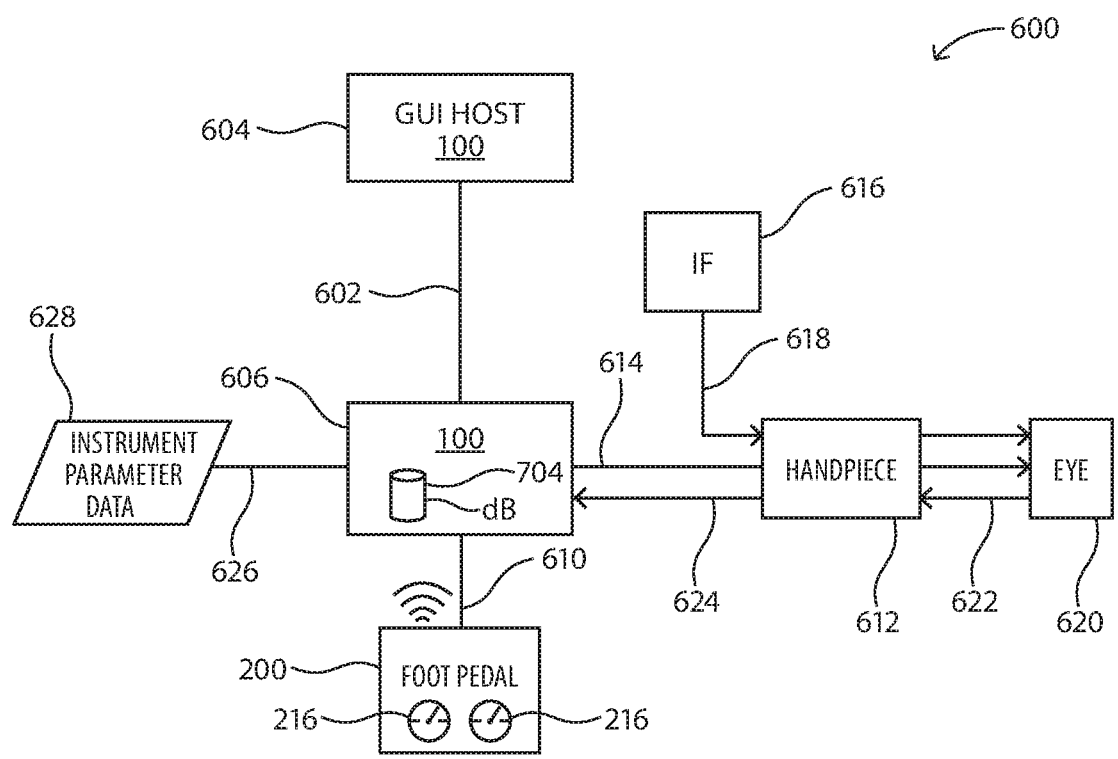
FIG. 2 is a diagram of an ophthalmic surgical console according to the embodiments.

As illustrated in FIG. 2, one peripheral that may communicate using peripheral communications bus 135 is a footpedal. The actuation of the foot pedal 200 by, for example, a user's foot, may have corresponded thereto by the actuation a travel distance, which may be visually indicated on at least one graphical user interface (GUI) 604 of the phacoemulsification system 600 communicatively associated with the foot pedal 200. The system may employ the computer system 100 discussed above, by way of example.

Moreover, the programmable travel positions of the foot pedal 200 may control different functions provided by the console 606, and/or may be additive in functionality. For example, a first travel position for foot pedal 200 may be programmed to have the console 606 provide a specific ultrasonic power function, a second position may add an irrigation function, and a third position may add another function. In addition, other switches 216 may allow for control of the functions activated via the foot pedal 200. For example, if an aspiration function is activated, at least one other switch 216 may be programmed to control the strength of the vacuum applied.

Although the present foot pedal control may be used in various surgical environments and applications, a particularly useful application is in an ocular surgical system, such as a phacoemulsification/vitrectomy system. In an exemplary phacoemulsification system 600, a serial communication cable 602 may connect a GUI 604 and console 606 for the purposes of controlling the console 606 by the GUI host 604. The console 606 may be considered a computational device in the arrangement shown, but other arrangements are possible. A switch module associated with an exemplary foot pedal 200, such as described herein, transmits control signals relating internal physical and virtual switch position information as input to the console 606 over a serial communications cable 610, or wirelessly if desired.

The system 600 has a handpiece 612 that typically includes a needle and electrical means, such as a piezoelectric crystal, for ultrasonically vibrating the needle. The console 606 supplies power on line 614 to the operative tip 612. An irrigation fluid source 616 can be fluidly coupled to operative tip 612 through line 618. The irrigation fluid and ultrasonic power are applied by the operative tip 612 to an eye 620, or other affected area or region. Alternatively, the irrigation source may be routed to the eye 620 through a separate pathway independent of the handpiece. Aspiration is provided from the eye 620 by one or more pumps (not shown), such as a peristaltic pump and/or venturi pump, via the console 606, through lines 622 and 624. A surgeon/operator may select modes of operation of the foregoing, and variables within each mode, via the GUI, using the foot pedal, and/or by voice command, by way of non-limiting example.

An interface communications cable 626 connects to the console 606 for distributing instrument data 628, and may include distribution of instrument settings and parameter information to other systems, subsystems and modules within and external to console 606. Although shown connected to the console 606, interface communications cable 626 may be connected or realized on any other subsystem (not shown) that could accommodate such an interface device able to distribute the respective data.

The disclosed embodiments may provide at least customizable, non-linear "custom modes" for emulsification in ophthalmic surgery, such as for phacoemulsification surgery performed using the foregoing console and footpedal, for example. More particularly, footpedal 200 may be used to indicate various custom operations for the handpiece 612. These custom operations may be corresponded to particular positions for footpedal 200 in or by the operative program operating on console 606, such as using one or more databases 704 associated with the programming on console 606.

The timing and power variance between the aforementioned custom (and any non-custom) zones may be defined by the user. For example, the user may select a set of values, such as the foot pedal treadle percentage in a particular zone, such as in "use-zone 2" (variable "X") of the footpedal 200, which may then be algorithmically corresponded to a power level 614 percentage of ultrasonic tip 612 (hereinafter, variable "Y") for timing within a certain zone prior to changeover to another zone. That is, the algorithms discussed throughout may interrelate the values X to the values Y based on a set point (X1, Y1), and the function provided by the algorithms may vary in different use zones. Accordingly, the value set may be applied to algorithmically calculate the slopes and trajectories, i.e., the mathematical function, of the Y values dependent on the X values, which slopes and trajectories may differ upon crossover between the zones discussed throughout.

More particularly and in order to provide optimal control for ultrasonic power delivery, various new power delivery modes are included in the embodiments, such as may be provided to the tip 612 via the console 606 responsive to actuation of the footpedal 200. By way of non-limiting example, the power modes may be divided into two categories, a user-definable "custom mode" and pre-defined modes, such as a pre-defined "progressive mode". Each "custom mode" may comprise interpolation algorithms, wherein the power delivery is broken into multiple segments defined by the user, such as to tailor to a particular region of footpedal 200 operation, such as in "zone 3," within which the surgeon may comfortably stay while effectively managing the range of power to optimally break up a cataract, by way of example.

The "progressive mode" may provide pre-defined algorithms to deliver ultrasonic power in a non-linear manner, such as may be selected by a surgeon. By way of non-limiting example, the pre-defined algorithms in this mode may gradually reach maximum power, or may acutely rise to 80 to 85% of the maximum power, and then gradually taper towards 100%. The surgeon may thus be able to choose from the aforementioned power delivery modes that best suit her surgical needs and techniques.

In an exemplary embodiment, custom mode may be a user-defined power delivery mode wherein the user selects, for example, two sets of values consisting of the desired foot pedal treadle percentage and the desired correspondent power percentage. Thereby, the power delivery may have corresponded thereto three distinct segments of power deliveries having different trajectories between 0 and 100% within the foot pedal treadle zone 3 (FP3), e.g. the zone of the foot pedal where power delivery occurs. Table 1 illustrates exemplary custom ultrasonic modes based on two user set points.

TABLE 1

| FP Zone Percentage | Custom Mode Example 1 | Linear | Custom Mode Example 2 | Custom Mode Example 3 |
|---|---|---|---|---|
| 0 | 0 | 0 | 0 | 0 |
| 5 | 16 | 5 | 3.125 | 30 |
| 10 | 32 | 10 | 6.25 | 60 |
| 15 | 48 | 15 | 9.375 | 90 |
| 20 | 64 | 20 | 12.5 | 90 |
| 25 | 80 | 25 | 15.625 | 90 |
| 30 | 80 | 30 | 18.75 | 90 |
| 35 | 80 | 35 | 21.875 | 90 |
| 40 | 80 | 40 | 25 | 90 |
| 45 | 80 | 45 | 25.625 | 90 |
| 50 | 80 | 50 | 26.25 | 90 |
| 55 | 80 | 55 | 26.875 | 91 |
| 60 | 80 | 60 | 27.5 | 92 |
| 65 | 80 | 65 | 28.125 | 93 |
| 70 | 82.85714286 | 70 | 28.75 | 94 |
| 75 | 85.71428571 | 75 | 29.375 | 95 |
| 80 | 88.57142857 | 80 | 30 | 96 |
| 85 | 91.42857143 | 85 | 47.5 | 97 |
| 90 | 94.28571429 | 90 | 65 | 98 |
| 95 | 97.14285714 | 95 | 82.5 | 99 |
| 100 | 100 | 100 | 100 | 100 |

The three segments may be formed using interpolation algorithms, such as based on user selection of start and end points, such as for the start and end of the middle segment. Algorithmically, (X1, Y1) and (X2, Y2) may be the start and end points provided for the two variables (i.e., power may be represented by variable Y, and foot pedal FP3 travel may be represented by variable X). Therefrom, three segments may be created, i.e., Start Segment prior to (X1, Y1), Performance Segment between (X1, Y1) and (X2, Y2), and Final Segment after (X2, Y2 Accordingly, the three segments may be interpolated from the two points provided by the user to create a segmented, customized power delivery trajectory, such as may be tailored to a surgeon's needs and comfort. By way of non-limiting example, the three segments may be defined and calculated as shown below, (wherein X is the desired FP3 percentage, Y is the desired power percentage, and FP3% is actual foot pedal treadle zone 3 percentage). Settings on the GUI may allow customization of MAX Power, X and Y.

If Actual FP3%<=defined X1, New FP3% may be calculated as:

Start Segment:

New Factor=(Y1/X1)*FP3%

If Actual FP3%>=X1 but<=X2, New FP3% may be calculated as:

Performance Segment:

New Factor=[1/(X2−X1)]*[(Y2−Y1)*FP3%+X1*Y2+X2*Y1]

If Actual FP3%>X2, New FP3% may be calculated as:

Final Segment:

New Factor=[1/(100−X2)]*[(100−Y2)*FP3%+100*(Y2−X2)]

The foregoing result may be used to calculate a firmware power value for the console as:

Firmware Power=New Factor*Max Power (from GUI)

To better illustrate the above algorithms, the following examples are provided. For example, the actual FP3% is at 10% and the user customized values in GUI may be:

Max Power=60%
Start Segment FP3% Limit X1=20%
Start Segment Power % Limit Y1=60%
Performance Segment FP3% Limit X2=80%
Performance Segment Power % Limit Y2=70%

Since actual FP3% is 10%, (10%<X1=20%), the Start Segment Algorithm may be:

New Factor=(Y1/X1)*FP3%
New Factor=(60%/20%)*10%=30%

Then calculate Power Value for Firmware:

Firmware Power=New Factor*Max Power
Firmware Power=(30%*60%)=18%

In another example, actual FP3% is at 50% and the user customized values in GUI are:

Max Power=60%
Start Segment FP3% Limit X1=20%
Start Segment Power % Limit Y1=60%
Performance Segment FP3% Limit X2=80%
Performance Segment Power % Limit Y2=70%

Since actual FP3% is at 50% (X1=20%=<50%=<X2=80%), the Performance Segment Algorithm may indicate:

New Factor=[(1/(X2−X1))]*[(Y2−Y1)(FP3%)+Y1*X2−Y2*X1]
New Factor=[(1/80−20))]*[(70−60)(50)+(60*80)−(70*20)]=65%
Firmware Power=New Factor*Max Power
Firmware Power=(65%*60%)=39%

In another example, actual FP3% is at 90% and the user customized values in GUI are:

Max Power=60%
Start Segment FP3% Limit X1=20%
Start Segment Power % Limit Y1=60%
Performance Segment FP3% Limit X2=80%
Performance Segment Power % Limit Y2=70%

Since Actual FP3 is at 90% (90%>X2=80%), the Final Segment Algorithm may indicate:

New Factor=[(1/(100−X2))]*[((100−Y2)(FP3%))+100*(Y2−X2)]
New Factor=[1/(100−80%)]*[((100−70%)(90%))+100*(70−80)]=85%
Firmware Power=New Factor*Max Power
Firmware Power=(85%*60%)=51%

Custom mode may allow for refined control of ultrasonic base power delivery, in a manner tailored to a surgeon's preferences and comfort, as mentioned above. Customized power delivery in custom mode may be combined with other available modes to produce additional unique power delivery modes. Interpolation of power data in custom mode may occur using two points, but may also be devised in general with any provided n points into (n+1) custom delivery segments. In short, the algorithm for any two consecutive points (Xm, Ym) and (Xn, Yn) forms a segment of power delivery as follows:

$$Y=[(Yn-Ym)*X+Xn*Ym-Xm*Yn]/(Xn-Xm)$$

Progressive mode, as mentioned above, may provide pre-defined power delivery algorithms in which the concentration of power delivery targets a preferred range, such as in the foot pedal "zone 3" region. By way of non-limiting example, if 40% to 80% of power is the most commonly used range for a particular surgeon, by selecting a new targeted power delivery for that range, the surgeon has substantially optimal control in the indicated range.

Additionally and in a non-limiting example, multiple categories of power delivery algorithms may be provided for selection of modes therewithin by the surgeon. For example, two categories, "slowmo" and "quickmo", in which a surgeon may choose a categorical mode to either slowly or quickly, respectively, increase the power, such as in a non-linear fashion, when pressing the treadle of the foot pedal, such as in the "zone 3" region. Exemplary slowmo and quickmo categorical modes are provided immediately below in Table 2. For a custom non-linear implementation, the user may not specify the Start Segment Limits in the GUI. Rather and by way of example, a slider may be provided to select one of several, such as seven, predefined Power Delivery Methods as pre-calculated below in Table 2.

and the last 20% of the FP3 region as a linear increase from 80% to 100% of full power. In relation to the foregoing examples, availability of variations for power delivery are helpful for surgeons who prefer to gradually increase the power after initial application, such as to avoid power over-use.

On the other hand and by way of example, in "quickmo" categories, upon entering the power region of the foot pedal treadle, modes may be provided in which ultrasonic power sharply rises before tapering gradually to maximum power. In a first algorithmic mode in this category, the first 20% of treadle travel may yield about 80% of the maximum power, with a gradual increase to the maximum power over the remaining depth of the treadle. Further refinement may also be available to provide three distinct levels of quickness (low, medium, and high).

TABLE 2

| | Slow-Mo Modes | | | | Quick-Mo Modes | | |
|---|---|---|---|---|---|---|---|
| FP Zone Percentage | Slow-Mo Low | Slow-Mo Medium | Slow-Mo High | Linear (Current Method) | Quick-Mo Low | Quick-Mo Medium | Quick-Mo High |
| 0 | 0 | 0 | 0 | 0 | 0 | 0 | 0 |
| 5 | 0.000313 | 0.125078 | 0.25 | 5 | 9.75 | 31.22499 | 43.068985 |
| 10 | 0.005 | 0.501256 | 1 | 10 | 19 | 43.5889894 | 58.642988 |
| 15 | 0.025316 | 1.1314 | 2.25 | 15 | 27.75 | 52.6782688 | 69.137092 |
| 20 | 0.080032 | 2.02041 | 4 | 20 | 36 | 60 | 76.837491 |
| 25 | 0.195504 | 3.175416 | 6.25 | 25 | 43.75 | 66.1437828 | 82.679728 |
| 30 | 0.405823 | 4.60608 | 9 | 30 | 51 | 71.4142843 | 87.172243 |
| 35 | 0.753149 | 6.32503 | 12.25 | 35 | 57.75 | 75.9934208 | 90.636292 |
| 40 | 1.288299 | 8.348486 | 16 | 40 | 64 | 80 | 93.29523 |
| 45 | 2.071774 | 10.69714 | 20.25 | 45 | 69.75 | 83.5164654 | 95.314938 |
| 50 | 3.175416 | 13.39746 | 25 | 50 | 75 | 86.6025404 | 96.824584 |
| 55 | 4.685062 | 16.48353 | 30.25 | 55 | 79.75 | 89.3028555 | 97.928226 |
| 60 | 6.70477 | 20 | 36 | 60 | 84 | 91.6515139 | 98.711701 |
| 65 | 9.363708 | 24.00658 | 42.25 | 65 | 87.75 | 93.67497 | 99.246851 |
| 70 | 12.82776 | 28.58572 | 49 | 70 | 91 | 95.3939201 | 99.594177 |
| 75 | 17.32027 | 33.85622 | 56.25 | 75 | 93.75 | 96.8245837 | 99.804496 |
| 80 | 23.16251 | 40 | 64 | 80 | 96 | 97.9795897 | 99.919968 |
| 85 | 30.86291 | 47.32173 | 72.25 | 85 | 97.75 | 98.8685997 | 99.974684 |
| 90 | 41.35701 | 56.41101 | 81 | 90 | 99 | 99.4987437 | 99.995 |
| 95 | 56.93101 | 68.77501 | 90.25 | 95 | 99.75 | 99.8749218 | 99.999687 |
| 100 | 100 | 100 | 100 | 100 | 100 | 100 | 100 |

More particularly, in the "slowmo" categories, modes may generally apply power gradually upon entering the treadle region controlling power, and may gradually increase power for the majority of the treadle region, such as until the last 20%-25% of the treadle region. Various algorithms may control the power delivery within a category of modes, such as one or more algorithms in each mode.

For example, one algorithm may limit the increase of power in a gradual manner until the last 25% of the treadle, at which point a sharp increase may be applied to reach the maximum power. Refinement may be included in the algorithm to achieve, for example, three distinct levels (i.e., low, medium, and high) of increase or decrease of power.

By way of additional example, control of power delivery may be further refined by defining the "control region" of gradual power increase as the first 80% of the FP3 region, In a second algorithmic mode within the quickmo category, the power may increase acutely in the initial 40% to 80% of the FP3 region, and may then increase in a linear fashion from 80% to 100% of the maximum power over the last 20% of the FP3. Modes in this category may be helpful for surgeons who prefer more significant power at the beginning of the treadle actuation in FP3, and a smooth range of targeted power to break up particles without the need to waver the treadle or substantially depress the foot pedal to its maximum to get to higher power.

Table 3, below, illustrates exemplary modes in accordance with the disclosed embodiments. In short, illustrated in Table 3 are algorithms and data supporting customized and progressive mode phacoemulsification power deliveries. For the progressive mode, Table 3 illustrates four variations (low, medium, high, and mixed) for the "slowmo" and "quickmo" modes.

TABLE 3

| Name | FP Zone3 Percentage Input | Percentage of Max Power Delivered Output | Status |
|---|---|---|---|
| Panel | 0 < X <= 100 | F(X) = 100 | Existing Mode |
|  | 1% to 100% | 100% |  |
| Linear | 0 < X <= 100 | F(X) = X | Existing Mode |
|  | 1% to 100% | 1% to 100% |  |
| Custom Mode |  |  |  |
| Custom Mode | 0 < (X1 < X2) < 100 | 0 <= (Y1 < Y2) = 100 | New Mode |
| Initial Seg | 0 < X <= X1 | F(X) = (Y1/X1) * X |  |
| Sweet Spot Seg | X1 < X <= X2 | F(X) = [1/(X2 − X1)*[(Y2 − Y1)*X + Y1*Y2 − Y2*X1] |  |
| Final Seg | X2 < X <= 100 | F(X) = [1/(100 − X2)]*[(100 − Y2) * X + 100(Y2 − X2)] |  |
| Progressive SlowMo Modes |  |  |  |
| SlowMo Low | 0 < X <= 100 | F(X) = 100 − SQRT (10^4 − (X/10)^4) | New Mode |
|  | 01% to 45% | 01% to 20% |  |
|  | 45% to 100% | 20% to 100% |  |
| SlowMo Med | 0 < X <= 100 | F(X) = 100 SQRT(10^4 − X^2) | New Mode |
|  | 01% to 60% | 01% to 20% |  |
|  | 60% to 100% | 20% to 100% |  |
| SlowMo High | 0 < X <= 100 | F(X) = (X/10)^2 | New Mode |
|  | 01% to 80% | 01% to 20% |  |
|  | 80% to 100% | 20% to 100% |  |
| SlowMo Mix | 0 < X <= 80 | F(X) = 2 * (100 − SQRT(10^4 − X^2)) | New Mode |
|  | 80 < X <= 100 | F(X) = X |  |
|  | 01% to 45% | 01% to 20% |  |
|  | 45% to 80% | 20% to 80% |  |
|  | 80% to 100% | 80% to 100% |  |
| Progressive QuickMo Modes |  |  |  |
| QuickMo Low | 0 < X <= 100 | F(X) − 2 * X − (X/10)^2 | New Mode |
|  | 01% to 45% | 01% to 70% |  |
|  | 45% to 100% | 70% to 100% |  |
| QuickMo Medium | 0 < X <= 100 | F(X) = SQRT(X * (200 − X)) | New Mode |
|  | 01% to 40% | 01% to 80% |  |
|  | 40% to 100% | 80% to 100% |  |
| QuickMo High | 0 < X <= 100 | F(X) = SQRT(10^4 − ((100 − χ)/10)^4) | New Mode |
|  | 01% to 20% | 01% to 80% |  |
|  | 20% to 100% | 80% to 100% |  |
| QuickMo Mix | 0 < X <= 80 | F(X) = SQRT(X * (160 − X)) | New Mode |
|  | 80 < X <= 100 | F(X) = X |  |
|  | 01% to 30% | 01% to 60% |  |
|  | 30% to 80% | 60% to 80% |  |
|  | 80% to 100% | 80% to 100% |  |

As an example, actual FP3% may be at 35% and custom values in the GUI may be:
Power Mode: Quick-Mo Low
Max Power: 100%
Using the algorithm for Quick-Mo-Low,
Firmware Max Power=2*FP3%−(FP3%/10)^2
Firmware Max Power=(2*35)−(35/10)^2=57.75=58
Firmware Max Power=58*%

Of course, the exemplary algorithms discussed herein and specifically illustrated in Table 3 may vary, and algorithms may additionally vary with equipment variations. For example, algorithms may vary with alternative combinations or arrangements of ramping or linear applications, with different components or component locations, with different spatial or temporal relationships, and so on. By way of example, additional algorithms may include more distinct arcs and curves for the application of ultrasonic power. More specifically and by way of non-limiting example, alternatives for progressive modes may include auto-adjustment among the levels of slowmo and quickmo, such as dependent upon an occluded tip and/or level of density of cataract as may be defined by a surgeon during diagnostics.

Using the power delivery modes discussed throughout, surgeons may achieve preferred power ranges faster without having to navigate linearly through undesired power ranges. In addition to avoiding such inefficiencies, the foregoing examples may reduce the time and heat/energy in the eye by getting to targeted power ranges more quickly in the FP3 region. Further, such custom modes, particularly if provided with a custom user-defined "sweet spot" within a specific range in the FP3 region, may provide more control in ultrasonic power delivery within a comfortable zone in the foot pedal treadle uniquely tailored for a particular surgeon. Moreover, the providing of various optional custom modes allows for the flexibility of different power trajectories in different cases.

The use of custom power delivery modes also enables a smooth transition from occlusion to post occlusion while applying more effective power to break up occluded particles. For example, if a surgeon uses a quickmo mode too quickly increase power to break up a cataract and the equipment tip becomes occluded, instead of switching to a linear power delivery mode a slowmo mode may be set as the occluded mode. A new higher power setting may accordingly be achieved at the same foot pedal position, without requiring the surgeon to ease off the foot pedal. And, if backing off to a lower power is desired, gently easing off the foot pedal may provide the lower power, rather than dramatically lifting the foot off the treadle.

Additionally, in phacoemulsification systems, custom modes may be used for purposes beyond strict in-surgery use-zones. By way of non-limiting example, custom modes may also be used to apply pump ramp, aspiration levels and vacuum levels, such as to allow modified aspiration and vacuum for broken up particles as compared to gradual aspiration and vacuum levels for bigger or harder to break pieces.

Figure 3:
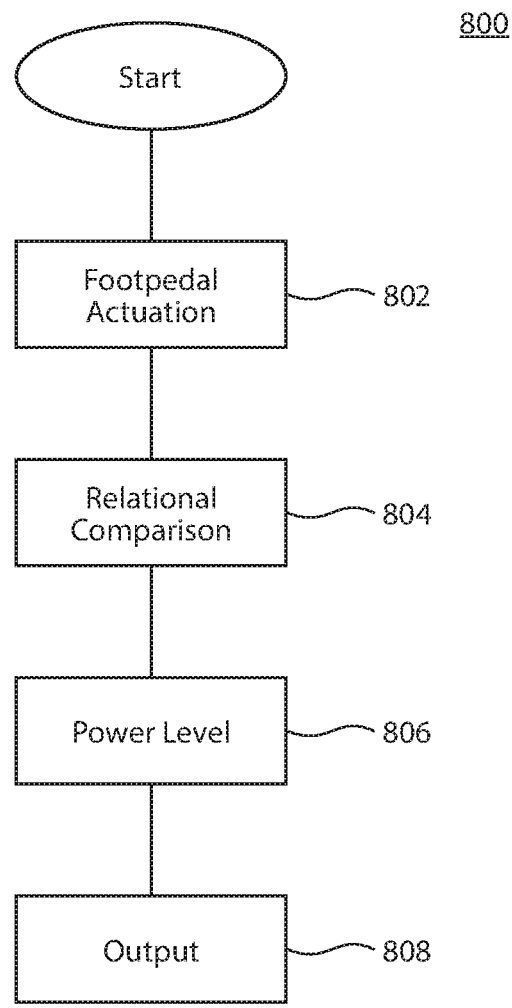
FIG. 3 is a flow diagram of a method according to the embodiments.

FIG. 3 is a flow diagram illustrating a method 800 of providing a customizable, non-linear "custom mode" for phacoemulsification in ophthalmic surgery. At step 802, a foot pedal actuation percentage is received. At step 804, the foot pedal actuation percentage is compared relationally to a custom zone algorithm, which is calculated from at least one user-indicated set point for ultrasonic power corresponded to particular foot pedal actuation percentages, and which is used to calculate a particular power level for a given foot pedal actuation percentage within the zone. At step 806, a foot pedal actuation percentage assessed as being in the custom zone is used by the algorithm for the custom zone to dictate the power level for the surgery. At step 808, the dictated ultrasonic power level is employed by the surgical console.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A phacoemulsification surgical console having a customizable non-linear custom phacoemulsification mode, comprising:
    an ultrasonic delivery tip;
    a foot pedal;
    non-transitory computing code resident on a computing memory associated with a computing processor which, when executed by the processor, causes to be executed the steps of:
    receiving a percentage actuation of the foot pedal;
    calculating, including from a non-linear algorithm, a percentage actuation for the ultrasonic delivery tip corresponding to the received percentage actuation of the foot pedal, wherein the non-linear algorithm comprises at least one set point of at least two user-defined parameters and a multiplicative factor applied to the at least one set point; and
    dictating the calculated percentage actuation for the ultrasonic delivery tip to the ultrasonic delivery tip.

2. The phacoemulsification console of claim 1, wherein the corresponding comprises utilizing a relational database.

3. The phacoemulsification console of claim 1, wherein the executed steps further comprise assessing, based on the received percentage actuation of the foot pedal, a desired operational zone.

4. The phacoemulsification console of claim 3, wherein the executed steps further comprise, based on a first condition of the desired operational zone having a first operational zone, the dictating the calculated percentage actuation for the ultrasonic delivery tip comprises dictating a calculated non-linear ultrasonic delivery tip percentage actuation.

5. The phacoemulsification console of claim 4, further comprising the step of, based on a second condition of the desired operational zone having a second operational zone, the dictating the calculated percentage actuation for the ultrasonic delivery tip comprises dictating a linear ultrasonic delivery tip percentage actuation.

6. The phacoemulsification console of claim 5, wherein the executed steps further comprise, based on a third condition of the desired operational zone having a third operational zone, the dictating the calculated percentage actuation for the ultrasonic delivery tip comprising dictating an ultrasonic delivery tip percentage actuation of zero.

7. The phacoemulsification console of claim 1, wherein the multiplicative factor applied to the at least one set point is back-calculated to the set point from a maximum power level for the ultrasonic delivery tip.

8. The phacoemulsification console of claim 7, wherein the at least one set point comprises at least two set points.

9. The phacoemulsification console of claim 1, wherein the non-linear algorithm comprises a start-segment calculation, a performance-segment calculation, and a final-segment calculation.

10. The phacoemulsification console of claim 9, wherein the start segment calculation obeys:

$$Y=(Y1/X1)*X$$

wherein Y is a calculated percentage power level actuation, X is the percentage actuation of the foot pedal, X1 is a percentage foot pedal set point, and Y1 is a power level percentage actuation set point corresponded to X1.

11. The phacoemulsification console of claim 10, wherein the performance segment calculation obeys:

$$Y=[(Y2-Y1)*X+Y1*X2-Y2*X1]/(X2-X1)$$

wherein Y2 is a second percentage foot pedal set point, and X2 is a second power level percentage actuation set point.

12. The phacoemulsification console of claim 1, wherein the non-linear algorithm further comprises a linear pre-start segment calculation.

* * * * *